United States Patent [19]
Naiman et al.

[11] Patent Number: 5,645,740
[45] Date of Patent: Jul. 8, 1997

[54] SYSTEM AND ASSEMBLAGE FOR PRODUCING MICROTEXTURIZED SUBSTRATES AND IMPLANTS

[76] Inventors: Charles S. Naiman, 160 Lancaster Ter., Brookline, Mass. 02146; Arthur Lamson, 16 Middle St., Westnewbury, Mass. 01895

[21] Appl. No.: 146,718

[22] Filed: Nov. 1, 1993

[51] Int. Cl.$^6$ .................................................. B23K 26/06
[52] U.S. Cl. ................... 219/121.68; 219/121.73
[58] Field of Search ................... 219/121.61, 121.62, 219/121.67, 121.68, 121.69, 121.73, 121.76, 121.78, 121.79, 121.8, 121.81, 121.83; 359/223, 225, 226

[56] References Cited

U.S. PATENT DOCUMENTS

| | | | |
|---|---|---|---|
| 3,549,733 | 12/1970 | Caddell | 219/121.69 |
| 4,475,027 | 10/1984 | Pressley | 219/121.73 |
| 4,673,409 | 6/1987 | Van Kampen | 219/121.71 |
| 4,749,840 | 6/1988 | Piwczyk | 219/121.68 |
| 4,778,469 | 10/1988 | Lin et al. | 623/16 |
| 4,791,267 | 12/1988 | Yokoyama et al. | 219/121.69 |
| 4,911,711 | 3/1990 | Telfair et al. | 219/121.83 |
| 4,940,508 | 7/1990 | Shamouilian et al. | 219/121.68 |
| 5,057,108 | 10/1991 | Shetty et al. | 606/53 |
| 5,246,530 | 9/1993 | Bugle et al. | 219/121.69 |
| 5,290,992 | 3/1994 | Lin et al. | 219/121.68 |

FOREIGN PATENT DOCUMENTS

| | | | |
|---|---|---|---|
| 0459394 | 12/1991 | European Pat. Off. | 219/121.78 |
| 57-25297 | 2/1982 | Japan | 219/121.78 |
| 4-200886 | 7/1992 | Japan | 219/121.68 |

*Primary Examiner*—Teresa J. Walberg
*Assistant Examiner*—Gregory L. Mills

[57] ABSTRACT

There is disclosed a system and assemblage for producing microtexturized surfaces on implants for use in vertebrate animals, including humans and on substrates for use in growing and developing tissues and/or cells in vitro. By using the disclosed system and assemblage, the geometric configuration and the dimensions of the microtexturized surfaces can be pre-determined to impart a customized design texture on the implant or substrate surface thereby optimizing implant acceptance by and durability in the host tissue and the in vitro promotion of the growth and development of various types of cell tissue on substrates.

5 Claims, 8 Drawing Sheets

SYSTEM AND ASSEMBLAGE FOR PRODUCING MICROTEXTURIZED SUBSTRATES AND IMPLANTS

INTRODUCTION

This invention is directed to a system and assemblage for creating microtexturized surfaces having pre-determined geometric configurations and dimensions on implants for use in verterbrate animals, including humans. Such texturized surfaces can also be provided on substrates which are used to grow and develop tissue cells in vitro and the cells thus grown can then be implanted in vertebrate animals, including humans. This invention also includes the microtexturized implants themselves as well as microtexturized substrates used to grow and develop tissues and/or cells.

BACKGROUND OF THE INVENTION

Many attempts have been made to produce orthopedic implants for humans that would be accepted by human host tissue for prolonged periods of time. Some implants often loosen due to the invasion of fibrous tissue while others loosen from the stress of mechanical forces and, eventually, they must be replaced. Other implants—because of the methods used to manufacture them—carry foreign debris when they are implanted which can promote inflammation and ultimately require their removal and replacement.

The response of tissue to any synthetic implant; i.e., any device that comes into contact with soft connective tissue or mineralized tissue, is related to the material used to make the implant, the surface chemistry of the implant and the surface microgeometry of the implant. The effects of tissue response to small changes in the surface chemistry and to small changes in the material used to make the implant are minimal, but such changes in surface microgeometry exert a strong influence on cell behavior.

For example, it has been established that, implants, having relatively high surface free energies as defined by contact angle studies exhibit better in vitro cell attachment and growth characteristics. It has also been established that implants having different surface free energies exhibit similar cell responses in the presence of serum proteins indicating that initial surface free energies are not a dominant factor in tissue response to implants in vivo. [J. Ricci, et al, *Bull. Hosp. Joint Dis. Orthop. Inst.*, 50(2), 126–138 (1990); J. L. Ricci, et al, *J. Biomed. Mater. Res.*, 18., 1073–1087 (1984); J. L. Ricci, et al, *J. Biomed. Mates Res.*, 25(5), 651–656 (1991); J. M. Shakenraad, et al. *J. Biomed. Mater. Res.*, 20, 773–784 (1986); P. vander Valk. et al. *J. Biomed. Mater. Res.*, 17, 807–817 (1983); T. A. Horbett, et al, *J. Biomed. Mater. Res.*, 22, 751–762 (1988); P. B. van Wachem, et al, *J. Biomed. Mater. Res.*, 21, 701–718 (1987)].

Surface microgeometry interaction between tissue and implant surfaces has been demonstrated on ceramic and metallic orthopedic implants. This interaction indicates that smooth implant surfaces promote the formation of thick fibrosis tissue encapsulation and that rough implant surfaces promote the formation of thinner, soft tissue encapsulation and more intimate bone integration. Smooth and porous titanium implant surfaces have been shown to have different effects on the orientation of fibrous tissue cells in vitro. In addition, surface roughness was demonstrated to be a factor in tissue integration into implants having hydroxyapatite surfaces and to alter the dynamics of cell attachment and growth on polymer implants whose surfaces had been roughened by hydrolyric etching. [J. M. Spivak, et al, *J. Biomed. Mater. Res*, 24, 1121–1149 (1990); J. L. Ricci, et al, "Modulation of Bone Ingrowth by Surface Chemistry and Roughness", *The Bone-Biomaterial Interface*, University of Toronto press, Toronto, Ont., Can., 334–349 (1991); T. Albrektsson, et al, *Acta. Orthop. Scand.*, 52, 155–170 (1981); T. Albrektsson, et al, *Biomaterials*, 6, 97–101 (1985); T. Albrektsson, et al, *Biomaterials*, 7, 201–205 (1986); K. A. Thomas, et al, *J. Biomed. Mater. Res.*, 19, 875–901 (1985); K. A. Thomas, et al, *J. Biomed. Mater. Res.*, 21, 1395–1414 (1987); B. Cheroudi, et al, *J. Biomed, Mater. Res.*, 24, 1067–1085 (1990); T. Inoue, et al, *J. Biomed. Mater. Res.*, 21, 107–126 (1987); U. M. Gross, et al, *Trans. Soc., Biomater.*, 13, 83 (1990); B. R. McAuslan, et al, *J. Biomed. Mater. Res.*, 21, 921–935 (1987)].

From the examination of in vitro growth characteristics of normal cells cultured on flat surfaces there has evolved the following cell "behavioral" characteristics:

attachment dependent growth; i.e., the dependence of normal diploid cells or substrate attachment for normal growth;

density-dependent inhibition; i.e., the tendency of such cells to slow or stop growing once a confluent monolayer is formed;

substrate-exploring function; i.e., the ability of some types of cells to migrate on a surface in search of acceptable areas for attachment and growth; and, contact guidance; i.e., the ability of some types of cells to migrate and orient along physical structures.

[J. L. Ricci, et al, *Trans. Soc. Biomat.*, 17, 253 (1991); J. L. Ricci, et al, *Tissue-Inducing Biomaterials*, Mat. Res. Soc. Symp. Proc, 252, 221–229(1992); J. Ricci, et al., *Bull. Hosp Joint. Dis. Orthop Inst.*, supra; J. L. Ricci, et al, *J. Biomed Mater Res.*, 25(5), Supra; M. Abercrombie, et al, *Exp. Cell, Res.*, 6, 293–306 (1954); M. Abercrombie, *Proc. Roy Soc.*, 207B., 129–147 (1980); D. M. Brunette, et al, *J. Dent. Res.*, 62, 1045–1048 (1983); D. M. Brunette, *Exp. Cell. Res.*, 164, 11–26 (1986); P. Clark, et al, *Development*, 108, 635–644 (1990)].

The behavioral characteristic of cellular contact guidance has been demonstrated in vitro on a variety of surfaces such as grooved titanium, grooved epoxy polymer, and collagen matrix materials of different textures and orientations. Grooved machined metal and polymer surfaces have also been shown to cause cellular and extracellular matrix orientation in vivo and be used to encourage or impede epithelial down growth in experimental dental implants. [B. Cheroudi, et al, *J. Biomed. Mater. Res.*, 24, 1067–1085 (1990) and 22, 459–473 (1988); G. A. Dunn, et al, supra; J. Overton, supra: S. L. Shor, supra; R. Sarber, et al, supra].

Substrates containing grooves of different configurations and sizes have been shown to have orientating effects on fibroblasts and substrates containing grooves of varying depths have been shown to have different degrees of effect on individual cell orientation establishing that grooved surfaces can modulate cell orientation in vitro and can cause oriented cell and tissue growth in vivo. For example, it has been shown that fibrous tissue forms strong interdigitations with relatively large grooves in the range of about 140 μm and can result in an effective barrier against soft tissue downgrowth perpendicular to the grooves. It has also been shown that smaller grooves on the order of about 3–22 μm were more effective in the contact guidance of individual cells. [D. M. Brunette, et al. *Development*, supra; P. Clark, et al, supra.]

These data have given rise to the development of several different types of implants. For example, U.S. Pat. No. 4,608,052 to Van Kampen discloses implants made from different compositions. The implants have attachment surfaces comprising a plurality of spaced posts and interconnecting, partially spherical, concave surfaces. The exemplified implants are stemmed femoral components which were produced using lasers to create posts having different geometric configurations. The implants are stated to be an improvement over smooth surfaced implants as the posts and concave surfaces permit interlocking tissue growth and intimate approximation with the implant surfaces to provide a relatively high degree of frictional "fit" between the implant and the human host tissue.

U.S. Pat. No. 5,002,572 to Picha discloses implants having texturized surfaces which are stated to be useful as mass transfer devices and which are intended to be implanted in soft tissue. The texturized surfaces of these implants comprise micro pillars having specified widths and spacing and minimum heights. The implants can be provided with means to deliver a therapeutic agent to the implant site to ward off infection and enhance tissue growth.

Implants also intended for use in soft tissue are disclosed in U.S. Pat. No. 5,011,494 to von Recum, et al. The texturized surfaces of these implants have a variety of geometric configurations comprising a plurality of projections and recesses formed in a three dimensional implant body. It is specified that the mean bridging, breadth and diametric distances and dimensions as defined are critical; i.e., a minimum defined depth must be present and the limiting dimension factor is the smallest, not the largest, dimension. It is also stated that the disclosed implants promote anchorage and the growth of collagen at the implant site "without causing encapsulation of the embedded portion of the device".

In general, the foregoing publications establish that cell attachment, growth, migration and orientation, as well as extracellular matrix synthesis and orientation, are moderated by substrate surface shape (i.e., microgeometry) as well as by surface chemistry. However, the findings in these publications do not address what effects different substrate microgeometrics and sizes would have on various cell colony growth and migration parameters as opposed to the morphology of individual cells. Thus, while these publications establish that surface microgeometry of implants influences cell orientation, they do not disclose or suggest what effect different surface microgeometry of implants would have on both the rate and direction of the cell colony growth of different cells and different tissues surrounding an implant.

Current methods used to texturize the surfaces of implants typically employ sand, glass bead or alumina grit blasting techniques and acid etching techniques of the implant surface. In sand, glass bead or alumina grit blasting techniques, compressed air is generally used to drive a blasting medium onto the implant surface at a high velocity in order to deform and, in some instances, remove portions of the implant surface. The surface texture obtained depends upon the size, shape and hardness of the implant material and on the velocity at which the blasting medium is driven onto the implant surface. The most common surfaces produced by sand or glass bead blasting are matte or satin-finishes while alumina grit blasting produces a roughened surface.

In acid etching techniques a pattern or mask is placed upon that surface of the implant desired to be texturized. The pattern or mask is then typically treated with an acid that corrodes the exposed surface of the implant whereupon the pattern or mask is removed and the acid treated surface is washed or neutralized with an appropriate solvent.

Illustrative of the sand or glass bead blasting technique is the method disclosed in U.S. Pat. No. 5,057,108 to H .R. Shetty, et al wherein the implant surface is shot blasted with metal shot followed by glass bead blasting and then electropolishing.

Illustrative of an acid etching technique is the method disclosed in U.S. Pat. No. 4,778,469 to R. Y. Lin, et al wherein an acid soluble (e.g., aluminum or zinc) space occupier is used. The space occupier contains the pattern to be transferred to the implant surface and is placed on the desired portion of the implant surface that is to be texturized. The space occupier is pressed into the implant surface and is then removed by treating it with acid. The materials used as implants are thermoplastic resins such as polyetheretherketone and polyphenylene sulfid.

It has been found that these typical blasting techniques leave debris from the processing materials embedded in the implant surface as contaminants. This debris has also been found in soft tissue isolated from the areas adjacent to failed press-fit total hip replacements indicating that the debris was released from the surface of the implant.

These problems of residual contaminant debris are overcome by using the system and assemblage of the invention which produces texturized implant surfaces without introducing embedded, particulate contaminants. In addition, the system and assemblage of the invention can be used to remove contaminants from implant surfaces that have been texturized by blasting employing optical and/or chemical lithography and acid etching techniques such as by ablating the treated surface. During ablation, the treated surface can also be annealed to enhance the fatigue properties of implants produced from metals.

SUMMARY OF THE INVENTION

It has now been found that the rate and direction of cell colony growth and the growth of different cell types surrounding an implant can be controlled and effected by using the implants of this invention produced by the system and assemblage of the invention. In general, the implants of the invention comprise a plurality of separate zones of texturized surfaces, each zone containing a different microgeometric design or pattern which is presented and exposed to the particular cell type for development of its unique colony growth. These different microgeometric texturized design surfaces are provided to:

(a) promote the rate and orient the direction of bone growth and discourage the growth of soft tissue to achieve secure fixation of the implant surfaces to bone tissue;

(b) promote the rate and orient the direction of the growth of soft tissue while discouraging the growth of bone tissue to achieve soft tissue integration with the implant surfaces; and, (c) create a barrier that discourages the growth of soft tissue, particularly soft fibrous tissue, and thereby prevent the migration of soft tissue growth into the bone tissue attachment surfaces of the implant.

In another embodiment of the invention, substrates having microgeometric texturized surfaces can be used to control the rate and orient the direction of the growth of different cells in vitro. After sufficient growth has been achieved, the particular in vitro tissue themselves can be transferred from the substrates and either implanted or used for other purposes such as in vitro cell research, growth of tissue and/or cells in bioreactors, and the like. For example, by employing microgeometric texturized surfaces on an appropriate substrate, epidermal cells can be grown for use in repairing or replacing tissue lost from burns, nerve cells can be grown for repairing or replacing damaged nerve tissue as well as glands, bone marrow, glial cells of neurological tissue, fibroblast cells, small vessel cells, smooth muscle cells, organ cells, and the like.

The implants of the invention can be provided from suitable and acceptable materials that are commercially available such as cast or wrought cobalt and chrome alloys, titanium-aluminum-vanadium alloys, stainless steel alloys, thermoplastic resins such as polyethoutherketone, polyphenylene sulfide, and the like, ceramics such as alumina, and the like, as well as combinations thereof.

In a further embodiment of the invention, a system and assemblage are provided to produce the microgeometric texturized implants and substrates of the invention by employing a high energy source to ablate the surfaces of the implants and substrates. In general, the system and assemblage comprise a source of controlled energy in the form of a radiated beam; means to direct the radiated energy beam along a predetermined route; means to alter the intensity of the radiated energy beam; means to focus the radiated energy beam onto the surface of the implant or substrate to be texturized; and, means to translate the focus of the radiated energy beam relative to the surface of the implant or substrate to produce pre-determined designs of microgeometric texturized surfaces in separate surface zones of the implant or substrate.

The controlled, radiated energy beam can be provided in the form of x-rays, ion beams, electron beams, optical beams such as lasers, and the like. These forms of energy can effectively ablate the surfaces of implants and substrates without leaving potentially harmful residue on their surfaces. All of these forms of radiated energy beams are conventional and are commercially available. For example, the conventional and commercially available lasers that can be employed include carbon dioxide lasers, neodymium-glass lasers, neodymium-yttrium-aluminum-garnet lasers both at a primary wavelength of 1.06 microns as well as at "doubled", "tripled" and "quadrupled" wavelengths of 0.52 microns, 0.35 microns and 0.26 microns, respectively, argon lasers, and the like. Preferably, an eximer laser is used in the system and assemblage of the invention to optimize performance results at an economically operable level.

In an additional embodiment, the system and apparatus of the invention can be used to remove contaminants from texturized implant surfaces that result from blasting and acid etching techniques. One method that can be employed to remove such contaminants comprises irradiating the surface to be cleaned with a beam of radiated energy having a wavelength that is absorbed by the contaminant but which is reflected by said surface to create loosened debris; and, removing the resultant, loosened debris.

For example, where a titanium surface has been texturized using sand, glass bead or alumina grit blasting techniques and particles of the blast media remain embedded in the titanium substrate, an infrared laser beam can be employed having a wavelength that is absorbed by the embedded material but which is reflected by the titanium substrate. Subsequently, an air jet can be used to blow away the resultant, loosened debris. Typically, a $CO_2$ laser having a wavelength of about 10 microns or a CO laser having a wavelength of about 5.3 microns can be used for this application.

Where the contaminants to be removed result from texturizing a substrate using acid etching techniques, an ultra violet laser beam such as a nitrogen laser having a wavelength of about 337 nm or a He-Cd laser can be similarly employed to remove the contaminants and clean the substrate surface.

The various means used to direct the radiated energy beam, alter its intensity, focus it on the surface of an implant substrate, and translate its focus can all be provided by conventional and commercially available components such as suitable attenuators, homogenizers, illuminators, rotators, reflective/refractive means such as optical mirrors, wedges, prisms, gratings and the like. In addition, these components can be computer directed and controlled and the computer can be programmed by known techniques so that different pre-determined microgeometric texturized designs can be ablated in separate zones on the surfaces of the implant or substrate. Further, progress of the ablation of the implant or substrate surfaces can be monitored by using an appropriately equipped TV camera and monitoring screen.

DETAILED DESCRIPTION OF THE INVENTION

The embodiments of the invention will become more apparent from the ensuing description when considered together with the accompanying drawing wherein like reference numerals denote like parts and wherein.

Figure 1:
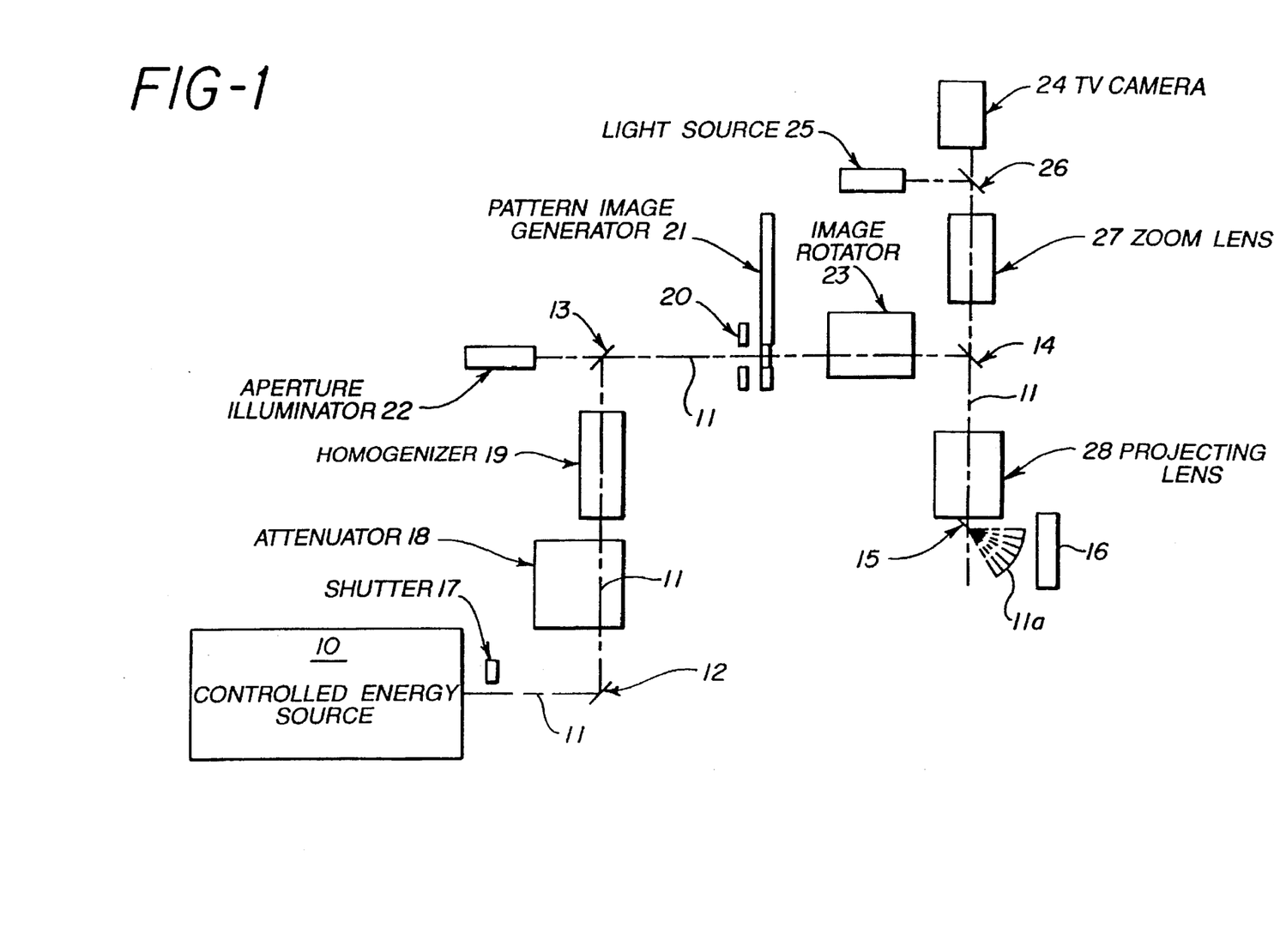
FIG. 1 is a schematic block diagram illustrating an assemblage that can be used in the system of the invention.

One assemblage that can be used in the system of the invention is illustrated in FIG. 1 wherein the source of controlled energy in the form of a radiated beam is supplied by an excimer laser 10 having a wavelength of 248 nm and whose optical beam is shown by dashed line 11. The path of beam 11 is directed and controlled by a plurality of optical mirrors 12, 13, 14 and 15. Mirror 15 directs beam 11 onto the surface of an implant or substrate 16 to create a microgeometric texturized surface of predetermined design as indicated by the plurality of beams 11a reflected from mirror 15.

In this assemblage, a shutter 17 is positioned at the output of laser 10 to provide a safety interlock as required by the Center for Devices and Radiological Health (CDRH) and to permit the laser to be warmed up and serviced without engaging the optical beam.

Downstream from shutter 17 and mirror 12, an attenuator 18 is positioned to intercept beam 11 and control the excitation voltage of laser 10. This permits the optical power output of laser 10 to be varied without affecting the optical properties of beam 11. Preferably, attenuator 18 is a variable attenuator which enables the fluence; i.e., energy densities (measured in Joules per square centimeter, $J/cm^2$), impacting the surfaces of the implant or substrate 16 to be varied over a range of about 10 to about 1.

From attenuator 18, laser beam 11 is preferably directed through an homogenizer 19 which serves to increase the uniformity of the intensity of laser beam 11 and maximize its usable fraction; i.e., that portion of laser beam 11 that performs its intended function which, in this instance, is ablation. Homogenizer 19 also serves to form laser beam 11 into a desired geometric shape; e.g., square, rectangular, circular, oval, elliptical, triangular, star-shaped, and the like, before it is passed through an aperture 20 to a mask carousel 21.

As beam 11 is directed through aperture 20 to mask carousel 21, an aperture illuminator 22 is engaged which enables an image having a pre-determined design or pattern to be projected onto the surface of the implant or substrate 16 in visible light before the implant or substrate surface is ablated. By passing the beam 11 through aperture 20, controlling only the desired portion of the pre-selected image projected onto the surface of the implant or substrate 16 can be effected.

Mask carousel 21 is equipped with a plurality of masks, each of which provide pre-selected line and space combinations to be imaged upon the surface of the implant or substrate 16. As the beam 11 exits mask carousel 21, it is directed through an image rotator 23 which turns the beam image being projected from the mask carousel 21 enabling any combination of lines and spaces to be imaged upon the surface of the implant or substrate 16. The image rotator 23 employed in this embodiment is a reflecting version of a Dove prism commonly referred to as a "K mirror". It serves to rotate the image exiting mask carousel 21 about its central axis without bending or distorting its central axis permitting infinite orientation of the exiting image so that a set of predetermined lines can be ablated in any direction.

In the embodiment shown, a TV camera 24, a light source 25 illuminating the surface of the implant or substrate 16 being ablated, a splitter mirror 26 for coaxial illumination, a zoom lens 27 and a projecting lens 28 are provided to enable the projected image pattern and surface of the implant or substrate 16 to be viewed in real time during ablation of the implant or substrate surface. In this embodiment, mirror 14 serves as a combiner and splitter in accepting and reflecting the imaged beam 11 from rotator 23 as well as the illumination from light source 25 and directs them through projecting lens 28 permitting the surface of the implant or substrate to be reflected and directed back through zoom lens 27 to TV camera 24 to accomplish real time ablation viewing; i.e., from about 8 to about 18 ns (nanoseconds).

Mirror 15, which directs the imaged beam 11a onto the surface of the implant or substrate 16, is movably mounted by conventional means so that it is capable of rotating and tilting to project the imaged beam 11a in any direction through from about 30° to about 90° relative to the longitudinal axis of the projecting lens 28. Mirror 15 is also mounted so that it can be retracted out of the path of imaged beam 11a enabling imaged beam 11a to be projected directly onto the implant or substrate surface 16. With mirror 15 movably mounted in this manner, an imaged beam can be projected to ablate the inner surfaces of U-shaped implants such as femoral components for knee replacements or the inner and/or outer surfaces of tubular or cylindrical substrates for use in promoting in vitro cell growth.

Figure 2:
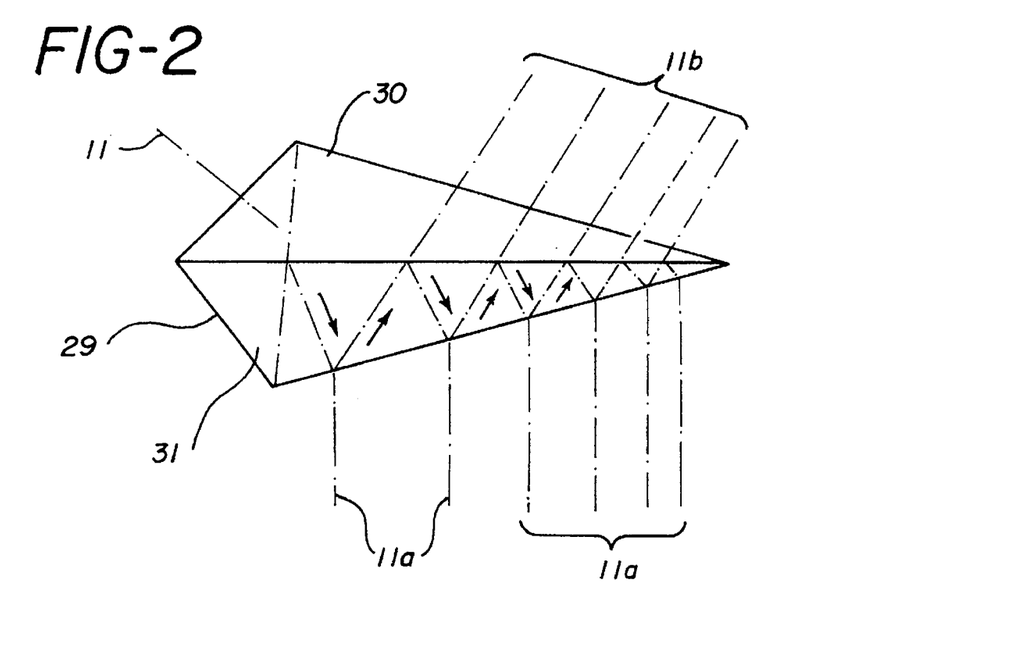
FIG. 2 is a perspective view of an optical prism that can be used in the assemblage of the invention.
Figure 3:
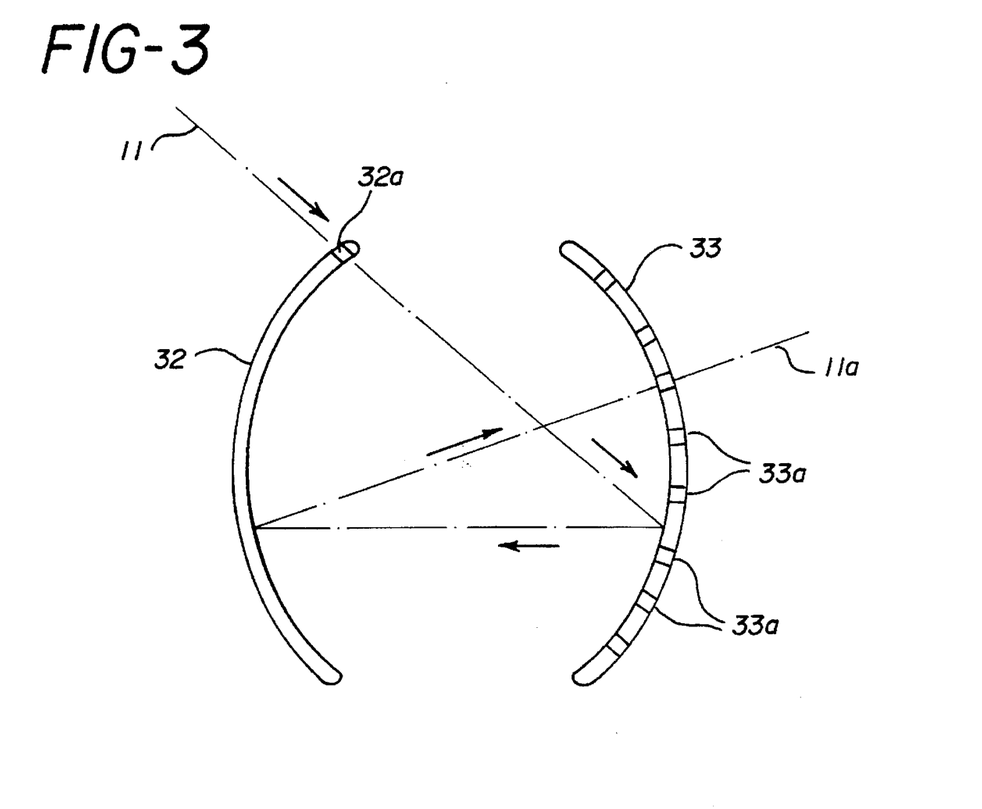
FIG. 3 is an exaggerated elevation view of optical mirrors that can be used in the assemblage of the invention.

Instead of employing a mask carousel 21 to create predetermined patterns or designs to be projected onto the surface of an implant or substrate, an optical prism or optical mirrors can be used as illustrated in FIGS. 2 and 3.

As shown in FIG. 2, a suitable optical prism 29 has a reflective surface 30 and a refractive surface 31. Prism 29 is positioned to receive optical beam 11 onto reflective surface 30. As optical beam 11 enters the prism 29 through reflective surface 30, it is refracted and reflected a number of times along the length of prism 29 in a path following the general direction of the small arrows. The number of times that beam 11 is refracted and reflected can be predetermined and calculated from the angle, size and index of refraction of the prism or other reflective/refractive means being used. A portion of optical beam 11 passes through refractive surface 31 in the form of a plurality of beams 11a which can either be directly projected onto the surface of an implant or substrate or be directed through an image rotator 23 as described above. A small percentage of optical beams 11a escape through reflective surface 30 shown in long dashed lines as 11b. Prism 29 can be mounted to rotate relative to optical beam 11 and optical beam 11 can also be scanned across surface 30 and/or down its length toward the apex of prism 29 to create any combination of lines and spaces in any direction as desired. Further, although a 3-faced prism is shown, multi-faceted prisms can also be employed to create more complex patterns and designs.

Opposed optical mirrors shown in FIG. 3 can also be used to produce pre-determined patterns and designs. In the arrangement shown in FIG. 3, a pair of concave mirrors 32, 33 are mounted so that their concave surfaces face each other. The surfaces of mirror 32 are treated to provide a window or port 32a and this mirror is positioned to enable optical beam 11 to pass through window or port 32a. The surfaces of opposed mirror 33 are treated to provide a plurality of windows or ports 33a. After optical beam 11 passes through window or port 32a, it is reflected and refracted a number of times between the opposed surfaces of mirrors 32 and 33 following a path indicated by the short arrows whereupon a portion of the reflected/refracted beams will pass through the plurality of windows or ports 33a in mirror 33. Either or both mirrors 32, 33 or optical beam 11 can be moved relative to each other to produce any combination of lines and spaces and thus create an infinite variety of desired patterns and designs. Gratings can also be used as the refractive/reflective means in place of the optical mirrors.

The assemblage of the system of the invention illustrated in FIGS. 1–3 can be readily operated using conventional computer hardware and software. A design data base can be developed for an implant or substrate from which import and export functions can be derived to convert data formats from conventional Computer Aided Design (CAD) programs. Specific microgeometric texturized design patterns can then be prepared and programmed for operation of the assemblage components. Typically, programming of a particular design pattern will be converted into explicit commands for integrated operation of the assemblage components and control of such functions as laser voltage, laser pulse trigger, shutter speed, attenuation, aperture rotation, mask selection, image rotation, mirror tilt and rotation positioning, and the like. For example, software information required to control an optical beam and provide the measurements to texturize a particular implant surface can be generated by a "Digitizing Beam" available from Laser Design, Inc.

Thus, the assemblage and system of the invention permits a plurality of different texturized microgeometric designs or patterns to be concurrently ablated on the surface of an implant or substrate and be provided in pre-designated areas on their surfaces to create separate microgeometric texturized zones. In addition, the system and assemblage of the invention enable ablated implant or substrate texturized patterns having a wide range of dimensions to be obtained such as from about 1 to 2 mm in diameter for dental implants to in excess of 225 mm in length for hip implants.

As mentioned above, the various components comprising the assemblage described in the embodiment of FIG. 1 are commercially available. For example, excimer lasers (10) can be obtained from Lambda Physik, Lumonics, Questek and Rofin Sinar; UV grade fused silica mirrors (12, 13, 14, 15) used for excimer image beam (11) and borosilicate or crown glass used for splitter mirror (26) can be obtained from Acton Research, CVI, and Spindler and Hoyer; attenuators (18) can be obtained from Lamson Engineering; homogenizers (19) for specific applications can be obtained from the Laser Technique division of Lambda Physik; aperture illuminators (22) and illuminating light sources (25) can be obtained from Leica, Melles Griot, Nikon, Oriel and Wild; a suitable TV camera (24) can be obtained from Hitachi, Panasonic and Sony; a suitable zoom lens (27) can be obtained from Ealing, Nikon, Oriel and Sony; and, a projecting lens (28) can be obtained from Ealing and Newport; optical prisms (29) and optical mirrors (32, 33) can be obtained from Rolyn Optics Co. and Reynard Enterprises, Inc.; and, gratings can be obtained from Lasiris, Inc. These commercial sources for the various components are obviously not intended to be exhaustive, but are mentioned merely as being representative and illustrative of their commercial availability.

Figure 4A:
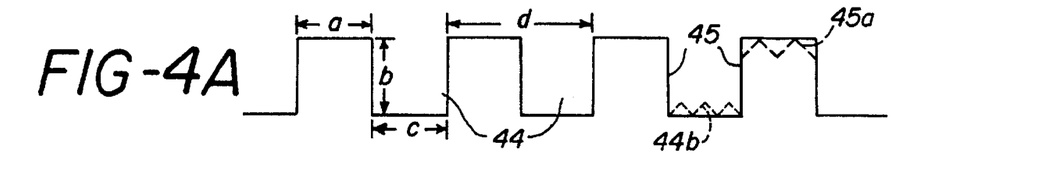
FIGS. 4A–4H are diagrammatic cross sectional views of microgeometric texturized configurations that can be used on the surfaces of hip implants and dental implants.
Figure 4B:
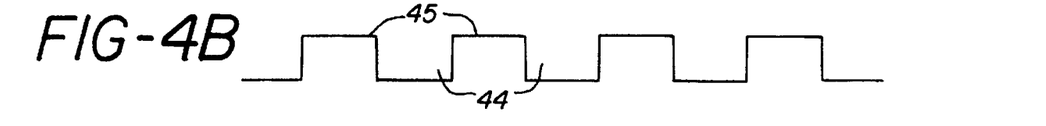
Figure 4C:
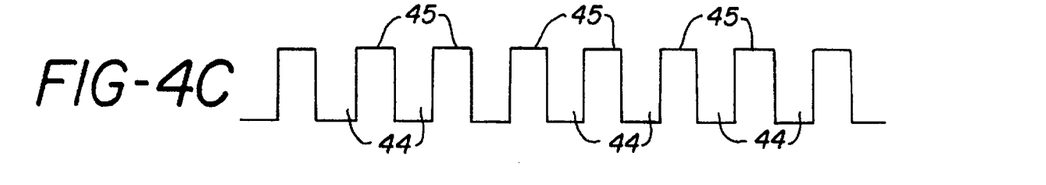
Figure 4D:
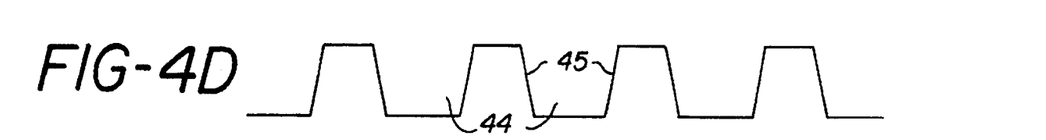
Figure 4E:
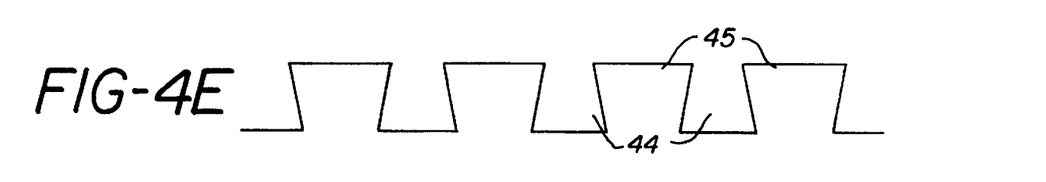
Figure 4F:
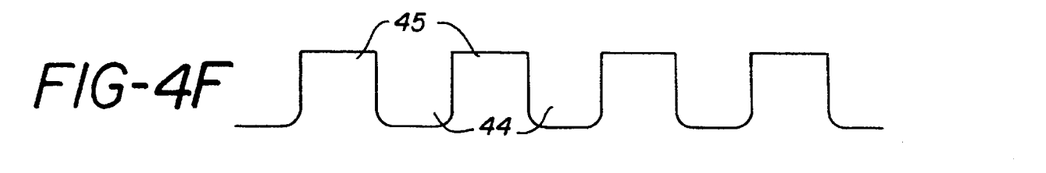
Figure 4G:
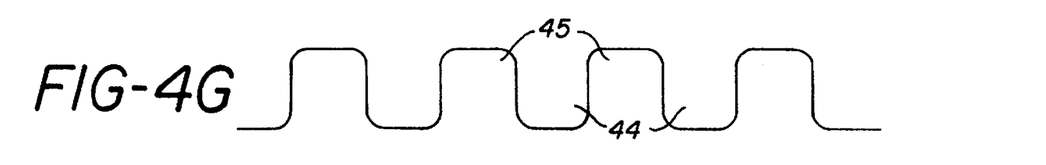
Figure 4H:
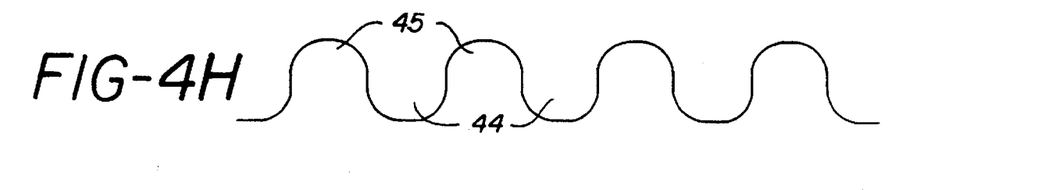

The microgeometric texturized configurations illustrated in FIGS. 4A–4H comprise a plurality of grooves 44 and ridges 45 formed by the system and assemblage of the invention and their dimensions are indicated by the letters "a", "b", "c" and "d". As can be seen, these configurations include those having square ridges 45 and square grooves (FIG. 4A) where "a", "b" and "c" are equal and where the spacing (or pitch) "d" between adjacent ridges 45 is twice that of "a", "b" or "c". FIGS. 4B and 4C illustrate rectangular configurations formed by grooves 44 and ridges 45 where the "b" dimension is not equal to that of "a" and/or "c". FIGS. 4D and 4E illustrate trapozidal configurations formed by grooves 44 and ridges 45 where the angles formed by "b" and "c" can be either greater than 90° as shown in FIG. 4D or less than 90° as shown in FIG. 4E. In FIG. 4F, the corners formed by the intersection of dimensions "b" and "c" have been rounded and in FIG. 4G, these corners as well as the corners formed by the intersection of dimensions "a" and "b" have been rounded. These rounded corners can range from arcs of only a few degrees to arcs where consecutive grooves 44 and ridges 45 approach the configuration of a sine curve as shown in FIG. 4H. In all of these configurations, either the planar surface of the ridge 45; i.e., the "a" dimension, or the planar surface of the groove 44; i.e., the "c" dimension, or both can be corrugated as shown by dotted lines at 45a and 44a in FIG. 4A.

In the microgeometric texturized configurations illustrated in FIGS. 4A–4H, the dimension of "a" can be from about 1.5 um to about 100 um and the other dimensions, "b", "c" and "d", can be determined from the "a" dimension.

Figure 5A:
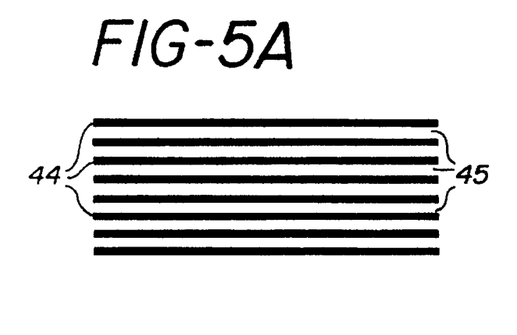
FIGS. 5A–5F are diagrammatic plan views illustrating various geometric patterns in which the microgeometric texturized configurations of FIGS. 4A–4H can be arranged.
Figure 5B:
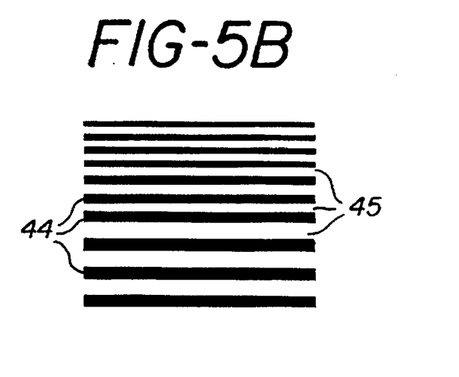
Figure 5C:
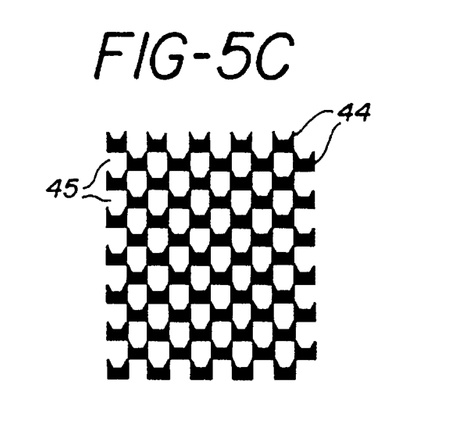
Figure 5D:
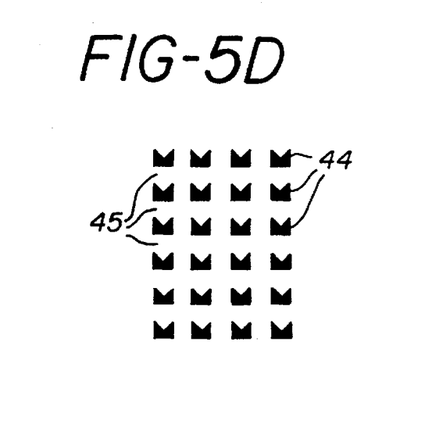
Figure 5E:
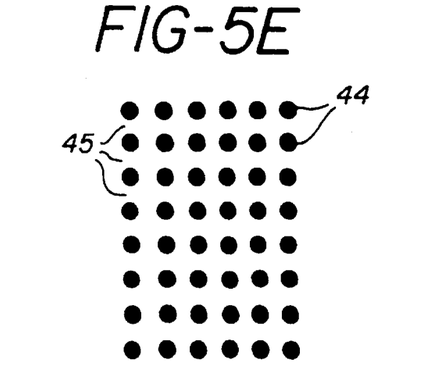
Figure 5F:
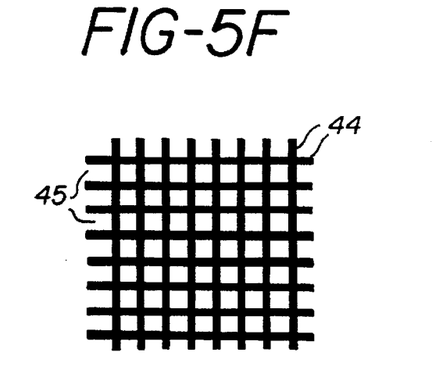

The geometric patterns in which the microgeometric texturized configurations shown in FIGS. 4A–4H can be arranged are illustrated in FIGS. 5A–5F. As can be seen, these unidirectional geometric patterns include those where the grooves 44 and ridges 45 are of equal size (i.e., "a"="c") and parallel (FIG. 5A); those where the grooves 44 and ridges 45 increase (or decrease) in size as shown in FIG. 5B; those where ridges 45 are in the form of individual projections defining a checkerboard configuration as illustrated in FIG. 5C; those where grooves 44 are depressed to define a plurality of spaced, parallel rectangular depressions (FIG. 5D) or a plurality of spaced, parallel circular depressions (FIG. 5E); and, those where the ridges 45 and grooves intersect one another as shown in FIG. 5F.

Figure 6A:
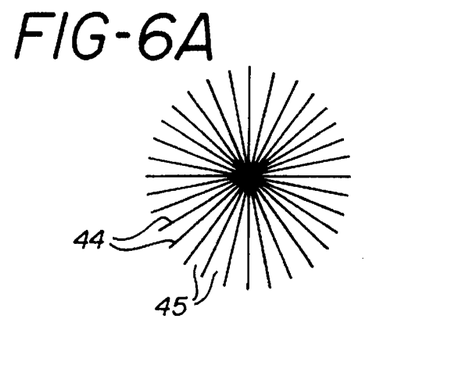
FIGS. 6A–6H are also diagrammatic plan views illustrating additional geometric patterns in which the microgeometric texturized configurations of FIGS. 4A–4H can be arranged.
Figure 6B:
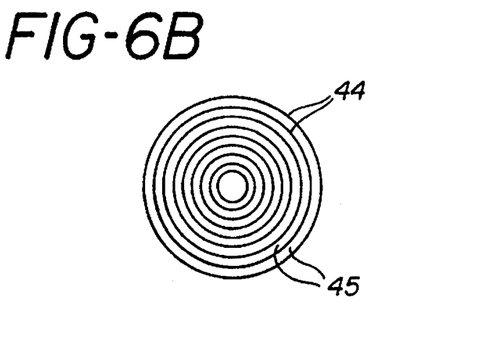
Figure 6C:
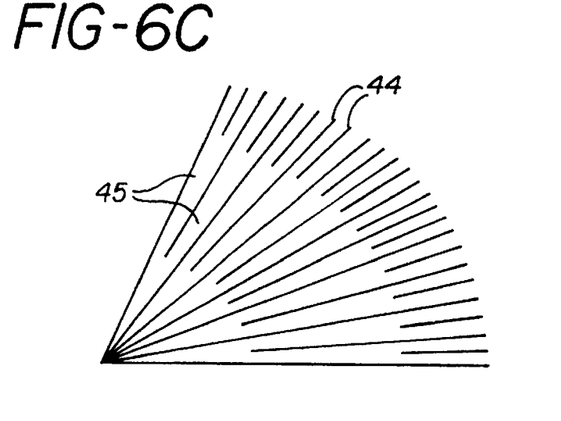
Figure 6D:
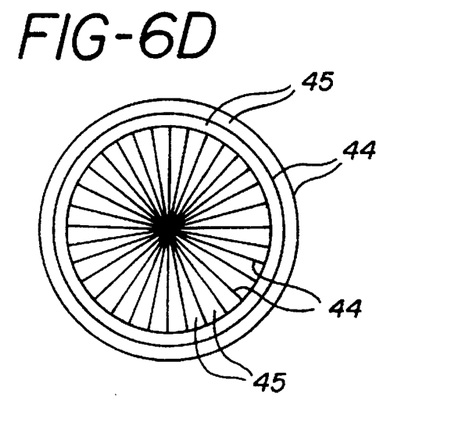
Figure 6E:
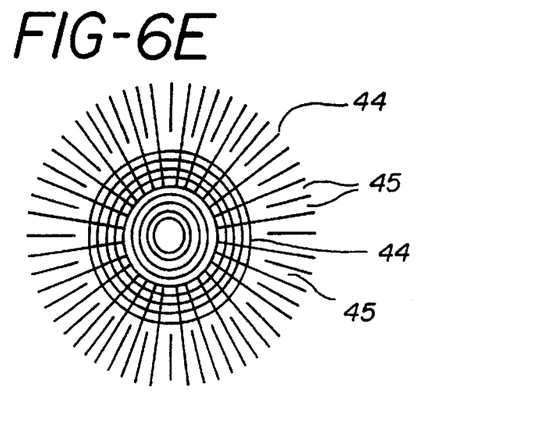
Figure 6F:
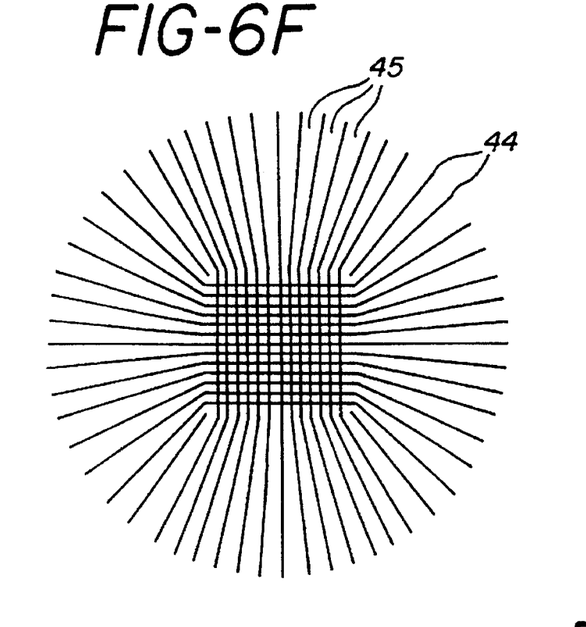
Figure 6G:
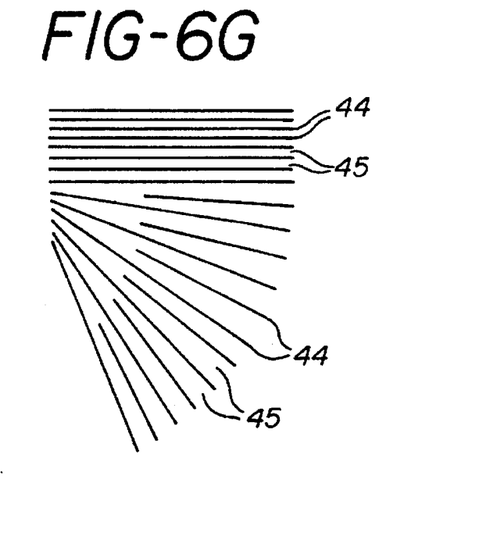
Figure 6H:
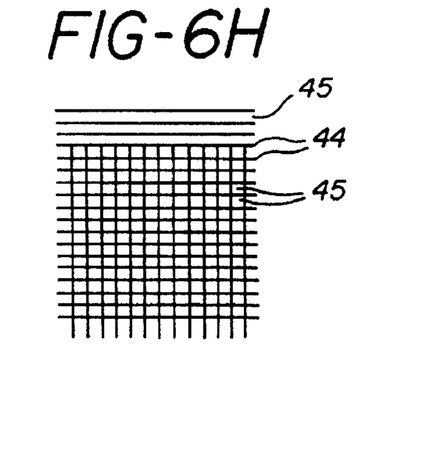

Additional geometric patterns in which the microgeometric texturized surface configurations can be arranged are illustrated in FIGS. 6A–6H in the form of unidirectional, arcuate and radial patterns as well as combinations thereof. As can be seen, these arrangements include radiating patterns (FIG. 6A); concentric circular patterns (FIG. 6B); radiating fan patterns (FIG. 6C); radiating/concentric circular patterns (FIG. 6D); radiating pattern intersecting concentric circular pattern (FIG. 6E); an intersecting pattern surrounded by a radiating pattern (FIG. 6F); a combination radiating fan pattern and parallel pattern (FIG. 6G); and, a combination intersecting pattern and parallel pattern (FIG. 6H).

From the embodiments illustrated in FIGS. 4A–4H, FIGS. 5A–5F and FIGS. 6A–6H, it will be appreciated that implants and substrates can be, provided with microgeometric texturized surfaces having a multitude of geometric patterns, designs, configurations and cross sections to select from for particular implants or substrate applications.

Figure 7A:
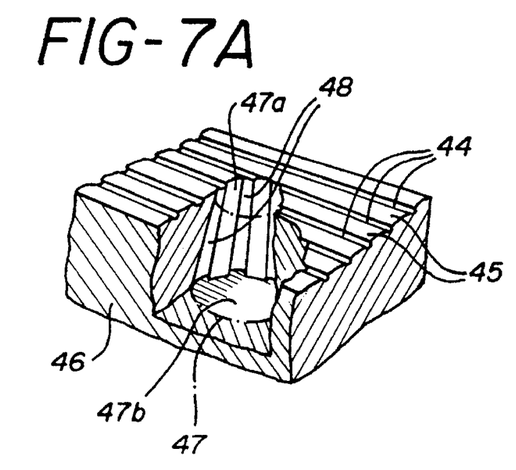
FIGS. 7A and 7B are perspective, fragmentary views, part broken away for clarity, of microgeometric surfaces illustrating embodiments of the configurations shown in FIGS. 4A–4H, 5A–5F and 6A–6H.
Figure 7B:
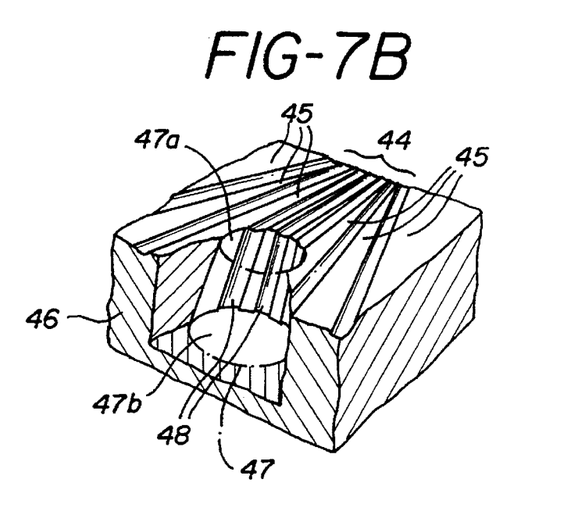

Embodiments illustrating some of these microgeometric texturized surface configurations are shown in FIGS. 7A and 7B wherein grooves 44 and ridges 45 are shown formed in the surface of a typical implant 46. In addition, a cavity 47 is shown formed in the body of the implant 46, the cavity 47 having an open top 47a and a closed bottom 47b. While cavity 47 can be of any geometric configuration, it is here shown in the form of a frustoconical shape, the circumference of open top 47a being larger than the circumference of closed bottom 47b. Further, the circumferential wall of cavity 47 can have a plurality of spaced, longitudinal grooves 48 formed therein.

In the embodiment shown in FIG. 7A, the geometric pattern of the grooves 44 and ridges 45 are formed in a parallel arrangement so that grooves 44 meet the upper ends of longitudinal grooves 48 at the open top 47a of cavity 47. With this arrangement, the direction of growth of tissues and cells can be oriented not only along grooves 44 and ridges 45 on the surface of the implant 46, but along grooves 48 down into cavity 47 so that the tissues and cells become anchored in the body of the implant 46.

Although the ridges 44 and grooves 45 illustrated in the embodiment of FIG. 7B are formed in a radial arrangement, grooves 44 similarly meet the upper ends of longitudinal grooves 48 to orient the direction of growth of tissues and cells along grooves 44 and 45 and down into cavity 47 along grooves 48.

Figure 8:
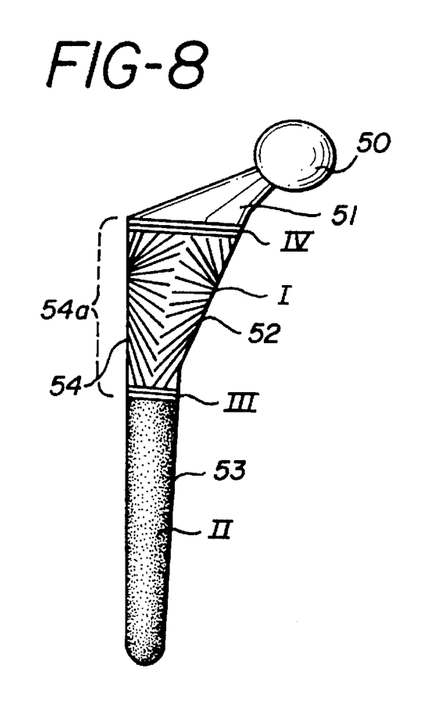
FIG. 8 is an elevation view of a hip implant having microgeometric texturized surfaces according to the invention.

A typical hip implant for humans having microgeometric texturized surfaces is illustrated in FIG. 8. As shown in FIG. 8 the implant comprises a femural head 50, a femural neck 51, a proximal stem 52 and a distal stem 53. Utilizing the system and assemblage of the invention, proximal stem 52 and distal stem 53 can each be ablated to create microgeometric texturized surfaces of different geometric designs or patterns in order to enhance and promote the growth of particular tissue. Premised upon the concept that oriented cells produce oriented tissue, selected portions on surface of the implant are not ablated to prevent migration of tissue growth from one part of the implant to another. Thus, four separate zones i.e., zones I, II, III and IV, are created on the implant surface. Zone I corresponds to the texturized surface on the proximal stem 52, zone II corresponds to the texturized surface on the distal stem 53 and zones III and IV represent barrier surfaces. The texturized surface in zone I on the proximal stem 52 is patterned to promote the rate and orient the direction of the growth of bone tissue on proximal stem 52 and the texturized surface in zone II on the distal stem 53 is patterned to promote the rate and orient the direction of the growth of soft tissue on the distal stem 53. Barrier zone III is provided to prevent migration of soft tissue growth into zone I of the proximal stem 52 and prevent migration of bone tissue into zone II of the distal stem 53. Barder zone IV is provided to prevent migration of soft tissue from the femural neck 51 into zone I of the proximal stem 52.

Where excessive stress is anticipated to be exerted on the lateral region 54 of the hip implant, it may be desirable to provide a reinforced hip implant where the lateral region 54 has been built up as indicated in dashed lines at 54a to impart additional strength to the implant. In either instance, the lateral region 54 or a built up lateral region 54a is preferably not ablated to act as an additional barrier zone in preventing migration of bone tissue growth from the proximal stem 52 into either lateral region 54 or built up lateral region 54a.

Implant surfaces ablated to have individual zones of different microgeometric texturized designs or patterns separated from one another by barrier zones provide implants that have good contact in the medial and lateral regions, but not in the anterior and posterior regions; achieve bone tissue fixation in the proximal region while preventing its migration into the distal region; and, prevent the growth of fibrosis tissue into the bone tissue attachment regions.

Figure 9:
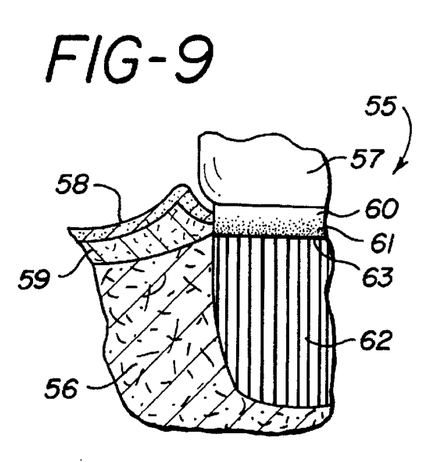
FIG. 9 is a fragmentary, enlarged elevation view illustrating a dental implant having microgeometric texturized surfaces according to the invention.

A typical dental implant whose surfaces have been microgeometrically texturized utilizing the system and assemblage of the invention is illustrated in FIG. 9. In FIG. 9, the dental implant, generally indicated by reference numeral 55, is shown seated in bone tissue 56 with the tooth portion 57 of the implant extending below the gingival epithelium tissue 58. Between the gingival epithelium tissue 58 and the bone tissue 56 is an area of soft connective tissue 59.

The surface of dental implant 55 that comes into contact with these three different types of tissue when the implant is embedded are ablated by the system and assemblage of the invention to have different microgeometric texturized patterns or designs for each distinct type of tissue. Thus, the surface of dental implant has a smooth zone 60 on the implant stem, a first microgeometric texturized zone 61, a second microgeometric texturized zone on the implant stem 62 and a barrier zone 63 between first and second texturized zones 61 and 62. Smooth zone 60 extends from the top of tooth 57 into and through the gingival epithelium tissues 58, partially into soft tissue 59 and blends into the first microgeometric texturized zone 61.

Smooth zone 60 promotes the growth and attachment of gingival epithelium tissue 58 to form a seal against oral environment. This zone 60 also deters the attachment of plaque to its surface while facilitating subsequent removal of any plaque that does accumulate on it. First microgeometric texturized zone 61 promotes the rate and orients the direction of the growth and attachment of soft connective tissue 59 and second microgeometric texturized zone 62 promotes the rate and orients the direction of the growth and attachment of bone tissue 56. Barrier zone 63 is provided to prevent the migration of soft connective tissue 59 into second zone 62 and prevent the migration of bone tissue 56 into first zone 61.

Figure 10:
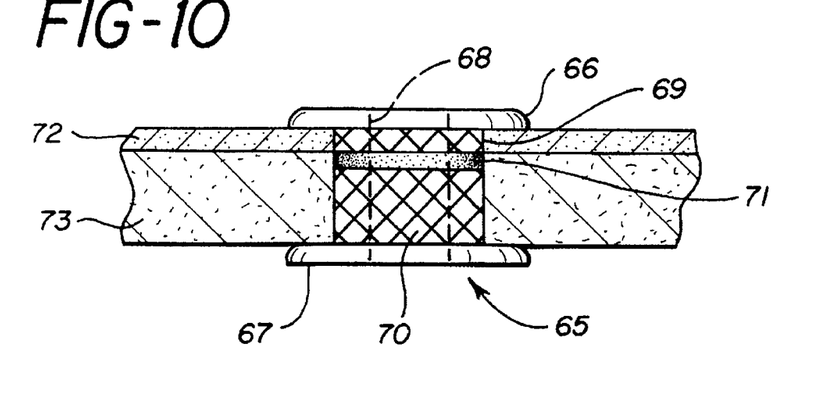
FIG. 10 is an elevation view, part in section, illustrating a transcutaneous implant having microgeometric texturized surface according to the invention; and, FIGS. 11 and 12 are perspective views, part broken away to reveal details, illustrating substrates that can be used to grow and develop various types of tissue cells in vitro.

The transcutaneous implant illustrated in FIG. 10, generally identified by reference numeral 65, is typically cylindrical having upper and lower flanges 66, 67 and a central longitudinal bore 68 that extends through the body of the implant 65 as indicated by the dashed lines. The outer circumferential surface of implant 65 is provided with a first microtexturized surface 69 and a second microtexturized surface 70 which are separated by a circumferential barrier zone 71.

Transcutaneous implant 65 is shown embedded in tissue consisting of epithelium tissue 72 and dermal and subdermal connective tissue 73. Microtexturized surface 69 promotes and orients the direction of growth of epithelium tissue 72 and microtexturized surface 70 promotes and orients the direction of growth of the dermal and sub-dermal tissue 73 into each other.

With transcutaneous implant 65 embedded in this manner, port 68 can be used as a passage to accomodate a tube for cholostomy containers or as a means to accomodate an electrode for pace makers, and the like.

To assure that the surfaces of the implants texturized by the system and apparatus of the invention are free from contaminants and debris, they can be examined using a scanning electron microscope equipped with a back scattered election imaging system and an x-ray micro-analysis system with a Quantum light element detector in conjunction with appropriate software for elemental analysis.

The texturized implants of the invention can be surgically implanted using known surgical techniques. For example, orthopaedic implants can be accomplished following the procedures described in *Campbell's Operative Orthopaedics*, edited by A. H. Crenshaw, published by C. V. Mosby, and dental implants can be accomplished following the procedures described in *Dental Implants*, edited by Charles Babbush, published by W. B. Saunders.

Figures 11, 12:
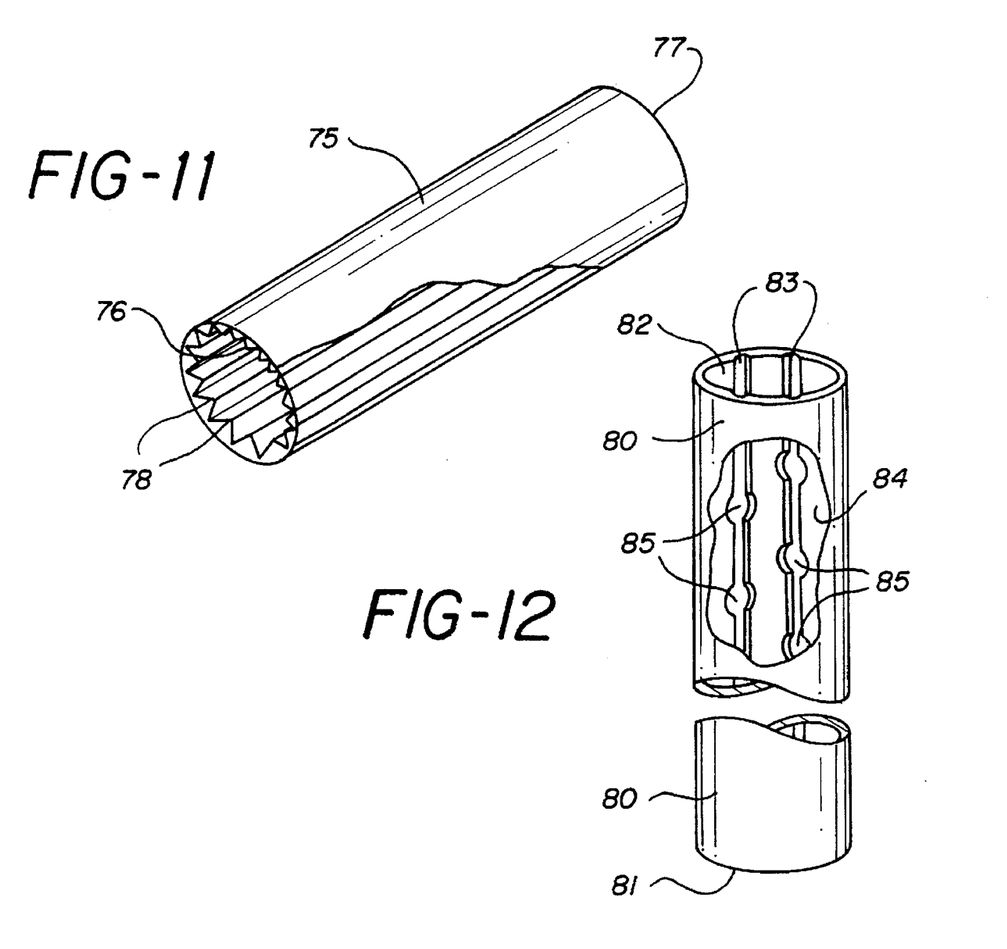

Representative substrates that can be used to promote and develop the rate and orient the direction of the growth of various types of tissue cells in vitro are illustrated in FIGS. 11 and 12. As shown in FIG. 11, one type of substrate that can be used can be provided in the form of a hollow cylindrical member 75 having opposed, open ends 76, 77 and a plurality of wedge shaped ridges 78 formed on its inner circumferential wall, the ridges 78 being parallel to each other and to the longitudinal axis of cylindrical member 75.

Another substrate embodiment is illustrated in FIG. 12 which is also in the form of a tubular member 80 having opposed open ends 81, 82 and a plurality of grooves 83 formed in its inner circumferential wall 84, the grooves 83 being parallel to each other and to the longitudinal axis of tubular member 80. In this embodiment, each of the grooves 83 also has a plurality of spaced, anchoring holes 85 formed along their lengths.

The microgeometric texturized designs and configurations on the substrates illustrated in FIGS. 11 and 12 can be combined in a single substrate or the substrates can be provided with the microgeometric texturized designs and configurations illustrated in FIGS. 4A–4H, 5A–5F and 6A–6H as well as various combinations thereof. In addition, substrates can be provided in the form of flat, planar members having one or more of these microgeometric texturized designs and configurations formed on their planar surfaces.

The efficacy of utilizing microgeometric texturized designs and configurations of the invention to promote and orient the direction of growth of tissues and cells is further illustrated by the following Example.

EXAMPLE

A. Substrate Fabrication

These studies of this Example were performed using a square wave shape (See FIG. 4A) and a flat surface as control (produced by the same methods), since the square wave shape has demonstrated a strong effect of cellular contact guidance in past studies [P. Clark, et al, *Development*, 108, 635–644 (1990)].

Following the nomenclature of Cheroudi et al [*J. Biomed. Master. Res.*, 24, 1067–1085 (1990)] for the surfaces, the distance comprising one groove and one ridge between the grooves is called the repeat spacing, or pitch (a+b, in Table 1). The depth (c in Table 1) of the groove refers to its deepest point, and the width (b in Table 1) is the total opening in the plane of the substrate.

The substrates used in these experiments have been molded from templates precision-fabricated at the National Nanofabrication Facility (NNF) at Cornell University. The investigators fabricated the templates with the assistance of the staff at NNF.

Fabrication of the microstructures by microlithography is a three-step process: design, application of a thin photoreactive layer, and development. To model a square-wave architecture, a window with parallel grid lines was designed on the CAD program Symbad and the CAD files were used to store different grid dimensions. Via a VAX station-3100, these files were transferred to an Optical Pattern Generator to fabricate a photomask from the design layout. This was done by exposing the window on a high-resolution emulsion plate with a laser interferometer. All photomasks were developed by typical film development procedures.

In the next step, 3-in. silicon wafers were coated with 15 μm of silicon dioxide, obtained by a mixture of 70% nitrous oxide and 17% silane gas, on a Chemical Deposition System. Deposition took place at a rate of 40 nm/min, with chamber conditions of 450 mtorr pressure, 50 W reflecting power, and 200° C. temperature. To align each grid window, the wafers were placed on a Projection Mask Aligner with their respective masks. For each template, there was a total of 239 exposures for 1.2 sec each. Exposure subsequently applied a thin layer of photoresist.

The development of square-wave microstructure was achieved by multiple reactive ion etching (RIE) techniques. Each template was initially placed on the Magnetron Ion Etcher where the silicon dixoide surface was etched with carbon tetraflouride at 1.0-kW peak voltage. Templates were next placed on the Barrel Etcher to strip the photoresist at 13.5 torr pressure and 240 ∞ C. temperature. The bare polysilicon surface was further etched with the Plasma Therm RIE System. This system etches in a directional manner, producing the square-wave shape used in this example. The parameters used were 49 parts/cm3 (pccm) chlorine and 7 pccm boron trichloride, 60 mtorr pressure, and 200 kW reflecting power. Finished templates were washed in hydrochloric acid and attached to 3-in-diameter aluminum stubs using epoxy to provide a rigid base. One-half of each template received an experimental microtexture, the other half was left flat.

Culture plate surfaces were created from the templates by solvent casting. The mold solution was obtained by dissolving 15 g of polystyrene in 100 mL ethyl acetate for at least 6 hr. A dam was produced by attaching tape around the perimeter of the template. An 8-mm solvent depth produce 0.5-mm, polystyrene substrates. After pouring the solvent on the template and before it dried, they were placed under high vacuum for 1 min to eliminate air bubbles at the interface, to avoid producing inconsistencies in the experimental surfaces. The solvent was allowed to dry for 24 hr and the surfaces were placed in a water bath for 5 hr. The substrates were peeled off their respective templates, and outer edges were removed to yield 50-mm circles. Substrates were allowed to dry for at least 24 hr to completely remove the solvent.

Surfaces were then evaporation-coated with titanium oxide in a Denton 502 Vacuum Evaporator. To obtain a 600-A coating, substrates were placed 100 mm from the electrodes under a 40-kW reflecting power and 5×10-5 mtorr pressure. Substrates were ethanol-sterilized for 5 min and attached to 50-mm petri dishes with a heated probe.

B. Preoaration of Rat Tendon Fibroblast (RTF) Cell Cultures from Explants

To initiate RTF cell cultures, hindfoot extensor tendons were removed from male, 14-dayold Sprague-Dawley rats that had been sacrificed by CO2 overdose. This method of sacrifice does not contaminate the tendon tissue. Four extensor tendons were removed under sterile conditions from each foot and placed in Hank's balanced salt solution (HBSS) containing 1% penicillin-streptomycin. The tendons were then separated from sheath tissue by microdissection. All culture procedures were conducted under sterile conditions. Cultures were grown in a 37° C. incubator in an atmosphere consisting of 95% air, 5% CO2, and saturated humidity. Cultures were maintained with Dulbecco's Modified Eagle's Medium (DMEM) containing 10% fetal bovine serum and 1% penstrep. The medium was carefully maintained at pH 7.4.

C. Subculturing Procedure for RTF Cell Cultures

Groups of explant cultures were grown for approximately 12–17 days; explants were removed, and the cultures were subcultured by enzyme digestion. Cultures were treated with a 0.25% trypsin solution in calcium- and magnesium-free HBSS for 20 min in order to free the cells from the culture plates. Cells were rinsed in medium containing 10% serum to stop the trypsin reaction, counted using a hemocytometer, and used to inoculate culture plates or initiate dot cultures. To ensure that the cells retained their in vivo behavior characteristics, only primary, secondary, and tertiary cultures were used for the experiments.

D. Preparation of Rat Bone Marrow (RBML Cultures from Rat Femurs

Cell cultures were prepared from 14-day-old rat femurs according to the method of Maniatopoulos [*Cell. Tiss. Res.*, 254, 317–330 (1988)]. In brief, femurs were dissected out under sterile conditions and the ends cut off. The marrow cavity was flushed out with medium using a syringe and the contents were incubated in a culture plate. While the hemopoietic elements do not attach, the stromal cells attach to the plate. After the unattached elements were removed, the attached cells were allowed to grow to confluency. The cells routinely stained positive for alkaline phosphatase activity. All experiments were conducted in DMEM with 10% fetal calf serum and 1% penstrep.

E. Subculturing Procedure for RBM Cultures

When these cultures became confluent, they were subcultured using the same procedure described in "C" above for the RTF cultures.

F. Initiation of Radiating "Dot" Cultures

RTF and RBM cells were embedded in a collagenous matrix as a source of cell colonies. These cultures were initiated by mixing cell suspensions with pepsin-digested type I bovine collagen solution. This solution was dispensed in 2-μL aliquots (containing 18,000–20,000 cells each) on the control and experimental substrates and polymenzed to form gels. Eight colonies were formed on each experimental substrate (designed to fit in a 60 mm culture plate) with four colonies placed on the flat control side and four colonies placed on the experimental microgeometry side. The resulting gel "dots" acted as sources of cells for colony formation. The cultures were maintained under standard sterile conditions in the appropriate medium.

Cultures were examined using an inverted-phase contrast microscope with a 35 mm camera attachment.

The "dot" culture model is basically an explant model with some important distinctions. While explant cultures can be used to measure cell colony formation of surfaces, they tend to form irregular colonies whose shapes cannot be easily analyzed. This is because the explants tend to be variable in shape, cell number and area of contact with the substrate. In the present model, colony formation begins from a circular dot of cell-containing collagen gel. Colony cell numbers and shapes are consistent and colony formation kinetics are consistent and easily measured. It is the consistency and measurability of this model that makes it appropriate for these experiments.

It is believed to be important to use freshly isolated cells for experiments such as these, since continuous cell lines, transformed cell lines, and cells that have been subcultured through many passages do not exhibit attachment and migration behavior that is true to their normal in vivo state.

G. Measurement of Radiating Cultures

Cultures were preserved in 10% phosphate buffered formalin on days 4 and 8 and stained with toluidine blue stain. Representative cultures were viewed and photographed using light microscopy in order to examine individual cells as well as colony outgrowth patterns. Using the Scientific Imaging Solutions computer workstation which consists of a light microscope with a videocamera connected to a personal computer with video acquisition hardware and TCL-Image image processing/image analysis software, images of the colonies were digitized and measured. Overall colony area and aspect ratios relative to the material surface microgeometry were recorded.

TABLE 1

Expected and actual dimensions of the square-wave microstructures

| Template | Expected Dimensions (μm) (a × b × c) | Actual dimensions (μm) (a × b × c) |
|---|---|---|
| 1 | 2.0 × 2.0 × 2.0 | 1.80 × 1.75 × 1.75 |
| 2 | 4.0 × 4.0 × 4.0 | 3.50 × 3.50 × 3.50 |
| 3 | 6.0 × 6.0 × 6.0 | 6.50 × 6.33 × 5.00 |
| 4 | 8.0 × 8.0 × 8.0 | 8.00 × 7.75 × 7.50 |
| 5 | 10.0 × 10.0 × 10.0 | 10.00 × 8.00 × 7.75 |
| 6 | 15.0 × 15.0 × 15.0 | 12.00 × 11.50 × 7.50 |

Note:
To simplify nomenclature, the substrates used in these studies are referred to as 2 μm (a = 1.80 μm), 4 μm (a = 3.50 μm), 6 μm (a = 6.50 μm), 8 μm (a = 8.00 μm), and 12 μm (a = 12.00 μm).

RESULTS

Characterization of Experimental Substrates: Analysis of Surface Microgeometry

The dimensions of the square-wave surface microgeometries were measured using the Scientific Imaging Solutions Workstation. Groove spacing was determined with the light microscope system, and this measurement was used to calibrate a scanning electron microscope (SEM). Depth of waves was determined by comparison of photomicrographs of the surfaces at 0° and tilted at a 45° angle. Observations from these instruments revealed slightly different microstructure dimensions than expected (see Table 1). Several steps in the microlithography process are believed to have contributed to this overall error. For example, the distance of the masks from the lens in the Projection Mask Aligner might not conform accurately to those set at its computer interface. Despite the departure from original dimensions, approximate square-wave microstructure was still obtained, since the etch depth, which is a function of the constant etch rate and time, was controlled. Note that the 15-μm depth could not be achieved by the suggested procedure because etching beyond 8 μm produced an uneven surface. Therefore, those templates with greater than 8 μm grids exhibit rectangular-wave shapes instead of square-wave shapes. Ti coupons were also processed by laser, achieving a wide variety of similar shapes.

I. Cell Colony Initiation

In this series of studies RTF and RBM cell colonies were grown on each of the six experimental and control substrates. RTF and RBM cells from the same animals were used to initiate groups of five to eight substrates per microgeometry type and cell type. Each surface had a flat area to act as an internal control. Four colonies each were initiated on the flat control and experimental sides of each 55-mm-diameter substrate. Thus, 40–64 colonies were initiated on each type of substrate for each cell type, divided between flat control surfaces and experimental microgeometry surfaces. The colonies analyzed in these experiments were fixed and quantitated at 4 and 8 days in order to document the most consistent period in colony growth. The RTF and RBM cell colonies were measured for area, x-axis growth (parallel to surface microgeometry), and y-axis growth (perpendicular to surface microgeometry). In order to correct for small variations in initial colony size and shape, which can be affected by the way the shape of the liquid collagen drop is influenced by surface microgeometry, average colony parameters at 4 days are subtracted from the 8-day data for each cell type and surface. This yields data expressed as area, x-axis, or y-axis increase between 4 and 8 days. X- to y-axis growth ratios and RBM cell vs. RTF cell growth ratios are also used to compare these results.

J. Cell Growth on Control Surfaces

Both cell types showed consistent growth by day 4, with the RTF cells showing earlier growth than the RBM cells. Examination of a 4-day-old RBM cell colony showed the central region, the original "dot," consisting of collagen and cels and cell outgrowth at the periphery with the cells oriented randomly and becoming sparse at the periphery. Both cell types showed extensive growth between 4 and 8 days, with the RTF cells growing at a faster rate than the RBM cells.

K. Cell Orientation and Migration

The experimental surfaces were observed to cause oriented cell attachment and migration, resulting in elongated colony growth which was accelerated in the x-direction (parallel to the surface microgeometry) and inhibited in the y-direction (perpendicular to the surface microgeometry). On an individual cell level, the cells were observed to orient along the surface grooves. This causes the cells to be "channeled" in the x-direction, as compared with control cultures, where the outgrowing cells move randomly on the flat surfaces. The most efficient cell "channeling" was observed on the 6-μm and 8-μm surfaces. On these surfaces, both cell types were observed to attach and orient within the grooves and on flat tops of the grooves. This resulted in enhanced x-axis growth and almost no y-axis growth by both cell types on these surfaces. On the smaller microgeometries, a different effect was observed. Both the RBM and RTF cells bridged the surfaces of the 2 μm grooves resulting in cells with different morphologies than those on the 6-, 8-, and 12 μm surfaces. These cells were wide and flattened and were not well oriented. On the 4μm grooves, the RBM and RTF cells showed mixed morphologies, with most cells aligned and elongated but not fully attached within the grooves. This resulted in appreciable y-axis growth by the RBM cells on the 2-μm surfaces and by the RTF cells on the 2- and 4-μm surfaces. At the other end of the size range, limited y-axis growth was also observed when these cell types were grown on the 12-μm surfaces. This may be a result of the microgeometry being significantly larger than the cell dimensions, allowing some diagonal cell orientation and cell "wraparound," resulting in limited y-axis growth.

L. Microgeometry Effects on Overall Cell Colony Growth

The results of the observed effects of these surfaces on overall RBM and RTF cell colony growth was very pronounced. All the experimental substrates caused varying but significant increases in x-axis growth compared to the diameter increase of the controls and varying but pronounced inhibition of y-axis growth. This nearly always resulted in suppression of overall growth of the RBM and RTF cell colonies compared with controls. The exception was RTF cell growth on the 2-μm surface which was equivalent in area increase to controls, presumably because of the y-axis growth contribution. Importantly, suppression of cell growth differed between cell types. This offers the opportunity to differentially provide a growth advantage to one cell type over the other.

M. The BaSis of Microgeometric Growth Control

The observed growth suppression is a geometric phenomenon. Circular control colonies increase in area as a function of the square of their radius. The colonies grown on the microgeometry surfaces become rectangular-to-oval in shape because of differential x- and y-axis growth rates. Since y-axis growth is extremely low in most cases, the colonies increase significantly in area only in the x-direction. This results in area increase based almost solely on linear increase in x-axis length. This one-dimensional growth (as compared to the two-dimensional growth of circular controls) results in a slower linear rate of area increase, even though its x-axis growth is faster than that of the control diameter growth.

N. Barrier Zone Surface-to Direct Growth of Fibrous Tissue

This surface should prevent y-axis migration and growth and orient fibrous tissue. While the maximal orientational effect (highest x-axis/y-axis ratio) on the RBM cells was observed on the 6-, 8-, and 12-μm surfaces, the maximal effect on the RTF cells was observed on the 8-μm surface. This indicates that the best microgeometry size to act as a barrier for RTF cell growth would be the 8-μm surface, since RTF cells grown on this surface would have the smallest y-axis growth across this surface and an enhanced directional growth in the x-axis to values nearly twice those of controls.

O. Surfaces for Stimulation of Fibrous Tissue Growth

Since fibrous tissue and bone cells will be "competing" for these surfaces in vivo, the ratio of RBM to RTF colony area increase on a given surface is an important parameter in surface selection. This ratio indicates the relative stimulation or inhibition of cell growth on these surfaces. Theoretically this ratio would be significant to provide advantage for growth of one or the other cell type on a surface, with high ratios favoring bone cell growth and low ratios favoring fibrous tissue growth. Based on these ratios, the 2 μm surface would provide a 32.8% decrease in RBM/RTF growth, providing a significant advantage in RTF cell growth. This surface could be used to favor RTF cell growth; it can also be used to significantly orient growth of these cells. The 4 μm surface provides a similar ratio but is based on lower overall growth rate. If nonoriented fibrous cell growth is required, the flat control surface provides an inherent advantage to RTF cells (a ratio of RBM to RTF cell growth of approximately 0.6). This effect has been observed in vivo where smooth surfaces have been shown to favor formation of thick fibrous tissue capsule formation as compared to textured surfaces of the same composition, which show less fibrous capsule formation and more extensive osteointegration.

P. A Surface for Stiumlation and Directional Conduction of Bone Growth

The surface with the highest ratio of RBM to RTF cell growth is the 12-μm substrate. The basis for the ratio is the fact that this surface inhibits RTF colony growth by 53.1% relative to controls. This is close to the maximal suppression of RTF cell growth seen on these microgeometries. This same surface, however, does not maximally suppress RBM cell growth (46.3% suppression relative to controls. This differential suppression results in a 14.4% increase in RBM/RTF growth ratio relative to the control ratio. In vivo, where both cell types are present and compete for growth, this provides a significant advantage to RBM colony growth. RBM cells grown on this surface also exhibit greatly enhanced directional growth in the x-axis. In vivo, this surface should favor bone over soft tissue growth and could be used to directionally conduct bone growth.

While the invention has been described with particularity and in some detail, it will be appreciated that changes and modifications can be made therein without departing from the scope of the invention recited in the appended claims.

What is claimed is:

1. An assemblage for producing pre-determined micro-geometric texturized designs on the surface of implants and substrates comprising:

(a) an excimer laser for producing an optical laser beam;

(b) at least a first optical mirror positioned to direct said optical laser beam to an attenuator capable of controlling the excitation voltage of said excimer laser and an homogenizer capable of maximizing the usable fraction of said optical laser beam and forming said optical laser beam to have a pre-determined, geometric cross section configuration;

(c) at least a second optical mirror positioned to direct said optical laser beam from said attenuator to a mask carousel having a plurality of masks, each of which defines pre-selected line and space combinations;

(d) at least a third optical mirror positioned to direct said optical laser beam from said mask carousel to a surface of said implant or substrate; and, (e) an aperture and aperture illuminator which, in combination, are capable of projecting a pre-selected segment of an image of said optical laser beam exiting from said mask carousel onto the surface of said implant or substrate.

2. An assemblage for producing pre-determined, micro-geometric texturized designs on the surfaces of implants and substrates comprising:

(a) an excimer laser that generates an optical laser beam;

(b) a first optical mirror positioned to direct said laser beam to an attenuator capable of controlling the excitation voltage of said excimer laser and to an homogenizer capable of increasing the uniformity of intensity and maximizing the usable fraction of said laser beam and forming said laser beam into pre-determined, geometric cross sectional configurations;

(c) a second optical mirror positioned to direct said laser beam from said homogenizer to a mask carousel having a plurality of masks, each of which defines pre-selected line and space combinations;

(d) an aperture and an aperture illuminator aligned with said mask carousel enabling a pre-selected segment of a laser beam image exiting from said mask carousel to be projected onto the surface of said implant or substrate;

(e) an image rotator aligned to receive the laser beam image exiting from said mask carousel;

(f) a third optical mirror positioned to direct said laser beam image from said image rotator to a movably mounted optical mirror; and, (g) means for rotating, tilting and retracting said movably mounted mirror to direct said laser beam image onto the surface of said implant or substrate to provide said pre-determined, microgeometric texturized designs on said surfaces.

3. The assemblage of claim 2 wherein the wavelength of said optical laser beam is 248 nm.

4. The assemblage of claim 2 wherein said attenuator is a variable attenuator capable of varying the impact fluence of said laser beam over a range of about 10 to about 1.

5. The assemblage of claim 2 wherein said image rotator is a K mirror capable of rotating said laser beam image about its central axis without bending or distorting its central axis.

* * * * *